United States Patent [19]

Bombardelli et al.

[11] Patent Number: 5,147,859
[45] Date of Patent: Sep. 15, 1992

[54] COMPLEXES OF GLYCERRHETINIC ACID WITH PHOSPHOLIPIDS AND PHARMACEUTICAL AND COSMETIC COMPOSITIONS CONTAINING THEM

[75] Inventors: Ezio Bombardelli; Gianfranco Patri; Roberto Pozzi, all of Milan, Italy

[73] Assignee: Indena S.p.A., Milan, Italy

[21] Appl. No.: 641,291

[22] Filed: Jan. 15, 1991

Related U.S. Application Data

[63] Continuation-in-part of Ser. No. 514,126, Apr. 25, 1990, abandoned, which is a continuation of Ser. No. 158,577, Feb. 22, 1988, abandoned.

[30] Foreign Application Priority Data

Feb. 26, 1987 [IT] Italy .................. 19496 A/87

[51] Int. Cl.$^5$ ................ A61K 31/705; A61K 31/575; A61K 9/127
[52] U.S. Cl. ..................... 514/26; 514/143; 514/177; 536/5; 536/6.2; 424/450; 554/80
[58] Field of Search ............ 514/26, 177, 143; 536/5, 6.2; 260/403; 424/450

[56] References Cited

FOREIGN PATENT DOCUMENTS

| | | |
|---|---|---|
| 0142193 | 5/1985 | European Pat. Off. |
| 0283713 | 9/1988 | European Pat. Off. |
| 1217547 | 5/1966 | Fed. Rep. of Germany .......... 536/5 |
| 59-42393 | 3/1984 | Japan ...................... 536/5 |
| 0887012 | 1/1962 | United Kingdom .................. 536/5 |

OTHER PUBLICATIONS

Shany et al.; Biochim. Biophys. Acta 307:83–91 (1973).
Pompei et al.; Nature 281:689–690 (1979).
Pompei et al.; Chemical Abstracts 92:191170n (1980).
Nakamura et al.; Chem. Pharm. Bull. 29(6):1681–1688 (1981).
Fukuda et al.; Biochim. Biophys. Acta 820:199–206 (1985).
Fukuda et al.; Biochim. Biophys. Acta 900:267–274 (1987).
Yu et al.; Chemical Abstracts 106:23158d (1987).
Proserpio; Chemical Abstracts 110:141220y (1989).
Takendouchi et al.; Chemical Abstracts 111:140222; (1989).
Tsuji et al.; Chem. Pharm. Bull. 39(4):1004–1008 (1991).

Primary Examiner—Ronald W. Griffin
Assistant Examiner—Nancy S. Carson
Attorney, Agent, or Firm—Bucknam and Archer

[57] ABSTRACT

Complexes of glycyrrhetinic acid with phospholipids are described in which the molar ratio of phospholipids to glycyrrhetinic acid is from 0.5 to 2. The phospholipids are selected from the group consisting of soy lecithins, phospholipids from bovine or swine brain or cutis, phosphatidylcholine, phosphatidylserine, phosphatidylethanolamine in which the acyl groups can be the same or different and are mostly derived from palmitic, stearic, oleic, linoleic, linolenic acids. The phospholipid may be soy phosphatidylcholine or distearoylphosphatidylcholine. Pharmaceutical compositions and a method for producing anti-inflammatory, antiulcer and healing effects in an animal are also described.

6 Claims, No Drawings

COMPLEXES OF GLYCERRHETINIC ACID WITH PHOSPHOLIPIDS AND PHARMACEUTICAL AND COSMETIC COMPOSITIONS CONTAINING THEM

This application is a continuation-in-part of U.S. Ser. No. 514,126, filed Apr. 25, 1990, which was a continuation of U.S. Ser. No. 158,577, filed Feb. 22, 1988. Both Ser. No. 514,126 and Ser. No. 158,577 have been abandoned.

The present invention relates to complexes of glycyrrhetinic acid with phospholipids, to a process for the preparation thereof and to pharmaceutical and/or cosmetic composition containing them.

Glycyrrhetinic acid is the aglycon of glycyrrhizic acid, and the main saponin constituent of *Glyccyrrhiza glabra* roots: it is endowed with anti-inflammatory, antiulcer and healing properties.

Its use has been restricted by short lasting action.

Now it has surprisingly been found that complexes with phospholipids of glycyrrhetinic acid allow a better bioavailability favouring a long lasting action.

The phospholipids that can be used according to this invention may be either vegetable or synthetic in nature, with acyl residues being the same or different, as shown by the formula:

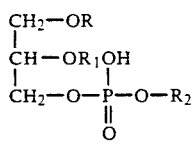

wherein R and $R_1$, which are the same or different, are mostly acyl residues of the palmitic, stearic, oleic, linoleic, linolenic acids, while $R_2$ is the residue of choline, ethanolamine or serine.

Particularly preferred phospholipids for use in cosmetics are then vegetable or naturally occurring phospholipids, such as those obtained from soy or from bovine or swing cutis or brain, similar to the ones that are found in human dermis; for other uses, a phospholipid which is chemically homogeneous and defined in its structure units (acyl and phosphoryl-amine groups) is preferred.

The complexes according to the invention are prepared by reacting glycyrrhetinic acid with the phospholipids in an aprotic solvent. The molar ratios of the phospholipid/glycyrrhetinic acid complex are in the range from 0.5 to 2, preferably about 1.

After solubilization has been completed, the complex compounds are isolated by removing the solvent under vacuum, by freeze drying or by precipitation with nonsolvents.

The complexes prepared according to the invention were tested pharmacologically: they proved to have a longer lasting activity than the corresponding free components.

Table 1 shows the results obtained in the Croton oil tests on the rates: it is clear that ghycyrrhetinic acid/phospholipids complex is significantly more active than the single components at 24 h after the administration. From the point of view of pharmaceutical and cosmetic technology, complexes obtained as above can be employed as microdispersions in water by preparing them by homogenization using high-speed stirrers or ultrasonic procedures, or they may be incorporated as such into appropriate pharmaceutical or cosmetic preparations.

For topical administration, it is convenient to use the above mentioned microdispersions, to which may optionally be added thickening agents, said and which may contain view wide percentages of active ingredient, from 0.1 to 30% and may also be incorporated in the form of gels or emulsions for dermatological or cosmetic purposes, or used alone. The complexes, due to their high lipophilia, may be dissolved in oils, in which they are stable, or incorporated in water/oil emulsions.

Advantageously, in view of the higher activity of the complexes according to the invention, the active ingredient dosage may, under certain circumstances, be reduced, the specific activity remaining unchanged.

Suitable forms for pharmaceutical and/or cosmetic uses by topical application, are creams, gels or aqueous microdispersions containing 0.1 to 30% by weight of glycycrrhetinic acid/phospholipid complex. These formulations may be administered one or several times daily, depending on the intended use.

The compositions according to the invention can in particular be used for treating conditions of inflammation and in general in all the fields in which activity of the glycyrrhetinic acid is recognized at present.

EXAMPLE 1

Preparation of the complex of 18 glycyrrhetinic acid with soy phosphatidylcholine 4.7 g of 18 glycyrrhetinic acid were suspended together with 8.8 g of soy phosphatidylcholine (Lipoid S-100) in 100 ml of methylene chloride, and the mixture was heated to mild reflux. When dissolution was complete, the solvent was removed under vacuum. 13.5 g of a vitrous solid were obtained, having $[\alpha]^{20} + 32°$ (c=1% in $CHCl_3$) and m.p. 184°–188° C.

EXAMPLE 2

100 g gel contain:

| | |
|---|---|
| Glycyrrhetinic acid/distearolyl-phosphatidylcholine | 2 g |
| Kathon | 0.2 g |
| Imidazolidine-urea | 0.4 g |
| Ethoxylated $C_8$–$C_{12}$ triglycerides | 25 g |
| Polyoxyethylen-20-oleylether | 6 g |
| Carboxyvinyl-polymer | 1.5 g |
| Triethanolamine | 2 g |
| Perfume | 0.2 g |
| Purified water | q.s. to 100 g |

TABLE 1

Anti-oedema effect of tested substances at different times
(Croton oil dermatitis in the mice ear, Tubaro et al., Agents Actions 17, 347, 1985)

| Substances | Dose µM/ear | 6 h | 9 h | 12 h | 18 h | 24 h |
|---|---|---|---|---|---|---|
| Glycyrrhetinic acid | 0.16 µM | 83.9 | 57.6 | 50 | 33.5 | 23.5 |
| Glycyrrhetinic acid/ Lipoid S-30• | 0.16 µM | 77.4 | 71.2 | 74 | 69.2 | 82.4** |
| Lipoid S-30• | 0.32 | 53.2 | 57.6 | 51.9 | 53.8 | 22.4 |

TABLE 1-continued

Anti-oedema effect of tested substances at different times
(Croton oil dermatitis in the mice ear, Tubaro et al., Agents
Actions 17, 347, 1985)

| Substances | Dose μM/ear | 6 h | 9 h | 12 h | 18 h | 24 h |
|---|---|---|---|---|---|---|
| μM | | | | | | |

**p 0.05 Student's t test
•Lipoid S-30 is a standardized mixture of soy-bean phospholipids.

We claim:

1. A complex of glycyrrhetinic acid with a phospholipid wherein the molar ratio of said phospholipid to glycycrrhetinic acid is between 0.5 and 2 and wherein said phospholipid is a member selected from the group consisting of soy lecithins, phospholipids from bovine or swine brain or cutis, phosphatidylcholine, phosphatidylserine, phosphatidylethanolamine, said phospholipid having the formula

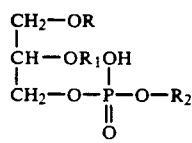

wherein R and $R_1$ are the same or different and each is a member selected from the group of the acyl group from palmitic, stearic, oleic, linoleic and linolenic acids and $R_2$ is the residue from chlorine, ethanolamine or serine.

2. The complex according to claim 1, wherein the phospholipid is soy phosphatidylcholine.

3. The complex according to claim 1, wherein the phospholipid is distearoylphosphatidylcholine.

4. A pharmaceutical composition containing as the active ingredient an effective amount of a complex of glycyrrhetinic acid with a phospholipid wherein the molar ratio of said phospholipid to glycyrrhetinic acid is between 0.5 and 2 and wherein said phospholipid is a member selected from the group consisting of soy lecithins, phospholipids from bovine or swine brain or cutis, phosphatidylcholine, phosphatidylserine, phosphatidylethanolamine, said phospholipid having the formula

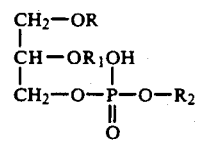

wherein R and $R_1$ are the same or different and each is a member selected from the group of the acyl group from palmitic, stearic, oleic, linoleic and linolenic acids and $R_2$ is the residue from choline, ethanolamine or serine.

5. The composition according to claim 4 wherein said phospholipid is a mixture of soybean phospholipids.

6. The method of treating an animal having inflammation which consists of administering to said animal an anti-inflammatory effective amount of a complex of glycyrrhetinic acid with a phospholipid wherein the molar ratio of said phospholipid to glycyrrhetinic acid is between 0.5 and 2 and wherein said phospholipid is a member selected from the group consisting of soy lecithins, phospholipids from bovine or swine brain or cutis, phosphatidylcholine, phosphatidylserine, phosphatidylethanolamine, said phospholipid having the formula

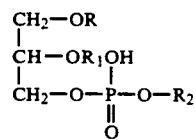

wherein R and $R_2$ are the same or different and each is a member selected from the group of the acyl group from palmitic, stearic, oleic, linoleic and linolenic acids and $R_2$ is the residue from chlorine, ethanolamine or serine.

* * * * *